(12) United States Patent
Winter et al.

(10) Patent No.: US 9,575,148 B2
(45) Date of Patent: Feb. 21, 2017

(54) METHOD FOR MR-GUIDED BRACHYTHERAPY WITH CONSISTENT PATIENT POSITIONING

(71) Applicant: IMRIS INC., Winnipeg (CA)

(72) Inventors: Jeff Winter, Winnipeg (CA); Meir Dahan, Winnipeg (CA); Labros Petropoulos, Winnipeg (CA); Brendan Guyot, Winnipeg (CA); Alexis Denis, Winnipeg (CA)

(73) Assignee: Imris Inc., Winnipeg, MB (CA)

( * ) Notice: Subject to any disclaimer, the term of this patent is extended or adjusted under 35 U.S.C. 154(b) by 707 days.

(21) Appl. No.: 14/072,397

(22) Filed: Nov. 5, 2013

(65) Prior Publication Data

US 2014/0180059 A1 Jun. 26, 2014

Related U.S. Application Data

(60) Provisional application No. 61/723,146, filed on Nov. 6, 2012.

(51) Int. Cl.
*A61N 5/10* (2006.01)
*A61B 5/055* (2006.01)
(Continued)

(52) U.S. Cl.
CPC ....... *G01R 33/3802* (2013.01); *A61N 5/1001* (2013.01); *A61B 5/0555* (2013.01);
(Continued)

(58) Field of Classification Search
CPC A61B 5/0555; G01R 33/3802; G01R 33/288; A61N 2005/1094; A61N 2005/1055; A61N 2005/1063; A61N 5/1001
See application file for complete search history.

(56) References Cited

U.S. PATENT DOCUMENTS 5,294,748 A * 3/1994 Schwenk ................. H02B 1/30
174/363
6,320,124 B1 * 11/2001 Cheng .................. H05K 9/0001
174/374
(Continued)

OTHER PUBLICATIONS

Wikipedia entry for "Brachytherapy", archived Oct. 31, 2011 and retrieved from <https://en.wikipedia.org/w/index.php?title=Brachytherapy&oldid=458379452> on Sep. 22, 2016.*

*Primary Examiner* — Long V Le
*Assistant Examiner* — Colin T Sakamoto
(74) *Attorney, Agent, or Firm* — Adrian D. Battison; Ade & Company Inc.

(57) ABSTRACT

In a method for guiding brachytherapy radiation treatment the patient is supported on a table and an MR magnet is brought into the treatment bunker through doors for imaging while the after-loader for the radiation source delivery is stored away in a storage location outside the RF shield. A safety system controls movement of the after-loader and the magnet. Images of the patient obtained while the patient is on the table are used to locate the applicator with respect to the lesion and organs-at-risk. The MR and X-ray compatible patient support table with MR coil integration includes a removable end-extension, which provides pelvic access for applicator insertion.

20 Claims, 4 Drawing Sheets

(51) Int. Cl.
*G01R 33/38* (2006.01)
*G01R 33/28* (2006.01)

(52) U.S. Cl.
CPC ............... *A61N 2005/1055* (2013.01); *A61N 2005/1063* (2013.01); *A61N 2005/1094* (2013.01); *G01R 33/288* (2013.01)

(56) References Cited

U.S. PATENT DOCUMENTS

| | | | |
|---|---|---|---|
| 7,908,690 B2 | 3/2011 | Luginbuhl | |
| 8,295,906 B2 | 10/2012 | Saunders | |
| 8,513,946 B2 | 8/2013 | Petropoulos | |
| 2002/0123681 A1* | 9/2002 | Zuk | A61B 5/055 600/410 |
| 2008/0039712 A1* | 2/2008 | Graves | A61B 5/055 600/411 |
| 2012/0112747 A1* | 5/2012 | Alexiuk | G01R 33/288 324/318 |
| 2014/0354279 A1* | 12/2014 | Dumoulin | G01R 33/422 324/318 |

* cited by examiner

METHOD FOR MR-GUIDED BRACHYTHERAPY WITH CONSISTENT PATIENT POSITIONING

This application claims the benefit under 35 USC 119(e) of Provisional Application 61/723,146 filed Nov. 6, 2012.

This invention relates to MRI guided brachytherapy radiation therapy.

BACKGROUND OF THE INVENTION

Brachytherapy involves the delivery of radiation dose via radioactive seeds within or adjacent to the tumour using either percutaneous insertion of needle applicators or insertion of intracavity applicator(s). A range of different applicators have been developed for several different tumour sites, including prostate, cervical, vaginal, rectal, esophagus, and lung. The applicator insertion is typically performed using ultrasound guidance or simply palpating the anatomy and guiding the applicator to the correct position.

Following the insertion of the applicator, x-ray images are typically acquired to determine the location of the applicator relative to the anatomy. However, increasingly, MR has been used in brachytherapy for imaging applicator placement and for treatment planning purposes. This move to MR has led to the development of MR-compatible applicators and accessories. The typical workflow for including MR in the brachytherapy process involves insertion of the applicators, moving the patient to the MR suite, and then once again moving the patient to another location for treatment.

Once the applicator is in place, the patient is moved to a radiation shielded bunker for high dose rate (HDR) treatment delivery, or a typical patient hospital room for pulsed dose rate (PDR) or low dose rate (LDR) treatments. For HDR therapies, the applicators in the patient are hooked up to long transfer tubes that connect to a remote after-loader device. The after-loader device provides a set of connections for the transfer tubes, through which the after-loader can move radioactive seeds (typically Co-60 or Ir-192) along the transfer tubes and into the applicators in the patient. The radioactive seeds stop at certain points along the applicator for predefined lengths of time to create a conformal dose distribution pattern. Once complete, the radioactive material is brought back along the transfer tube into the after-loader.

The main drawback of the MR inclusion in HDR brachytherapy today is that it involves moving the patient between the location of applicator insertion, MR imaging and treatment bunker. Some approaches have integrated the insertion of needles within the MR, using sophisticated tabletop designs or MR-compatible robotic systems. However, these approaches still require that the patient be transported between the MR and treatment bunker.

In U.S. Pat. No. 8,513,946 (Petropoulos) issued Aug. 20, 2013 filed May 14, 2010 assigned to IMRIS there is disclosed a "Movable table for Magnetic Resonance Imaging", which includes an embodiment of the invention with a pelvic region cut-out to provide access for pelvic procedures.

In U.S. Pat. No. 8,295,906 (Saunders) issued Oct. 23, 2012 and originally published Feb. 25, 2010 assigned to IMRIS there is disclosed the integration of MRI with radiation therapy.

U.S. Pat. No. 7,908,690 (Luginbuhl) issued Mar. 22, 2011 assigned to Sentinelle Medical there is disclosed an MR table top for MR-guided interventions called "Supine patient support for medical imaging.

The disclosures of the above patents are hereby incorporated herein by reference.

SUMMARY OF THE INVENTION

According to the invention there is provided a method for guiding brachytherapy radiation treatment of a lesion of a patient comprising:

supporting the patient on a treatment support table;

while the patient is supported on the support table, preparing the patient for radiation therapy on the treatment support table and moving an applicator for applying the brachytherapy radiation treatment to a treatment position at the patient;

providing an after-loader for supplying a radiation source to the applicator in a storage location having a storage door;

with the applicator located at the treatment position, moving the after-loader from the storage location to the applicator;

locating the treatment support table and the after-loader forming a radiation therapy treatment system in a treatment room;

providing an MRI system for imaging the patient including a cylindrical magnet;

moving the after-loader in the treatment room to the storage location spaced from the treatment support table;

providing an opening from an exterior magnet storage room into the treatment room with a magnet door on the opening;

with the after-loader moved to the storage location, moving the cylindrical magnet of the MRI system from the exterior magnet storage room outside the treatment room through the opening with the magnet door open into a position surrounding the treatment support table for obtaining images of the patient while on the treatment support table;

while the patient is on the treatment support table, using the MRI system to obtain a series of images of a location of the lesion and the applicator at the treatment position within the patient;

moving the magnet of the MRI system away from the treatment support table and out of the treatment room through the opening, and closing the magnet door so as to allow the radiation therapy;

providing a safety system to control movement of the after-loader and the magnet;

and using the images of the patient to locate the applicator with respect to the patient.

Preferably for treatment in the pelvic area, the treatment support table comprises a first main portion for supporting the upper body of the patient up to and including the pelvic region and a second removable portion extending from the pelvic region to the feet. The extension portion is preferably cantilevered from the end of the main portion and the main portion terminates at the extension portion leaving the area open for access by the physician.

Preferably the first main portion is arranged for attachment of stirrups for supporting the feet of the patient with the second removable portion removed such that the applicator is inserted by the physician to the required location with the second removable portion removed and the feet in the stirrups, where the stirrups can be carried on side rails of the first main portion.

In some cases the stirrups are removed and the second removable portion replaced for connection of the after-loader to the applicator for the treatment and the stirrups are removed for imaging.

Alternatively the stirrups can remain in place for imaging and are arranged for insertion into the cylindrical bore of the magnet. In this case the stirrups must be mounted in a manner which allows them to enter the bore and they must also be MR compatible.

Preferably patient with the applicator installed is imaged by the MR system to ensure proper location of the applicator.

Preferably the imaging and the brachytherapy radiation treatment are carried out without moving the patient relative to the treatment support table.

Preferably the treatment support table comprises an MR and X-ray compatible table with MR coil integration to allow efficient transitions from applicator insertion to MR imaging and to treatment delivery.

Preferably the safety system is arranged to prevent the after-loader from being brought from the storage location into the treatment room while the MR is in the treatment room.

Preferably there are provided MR coils designed for integration into the treatment support table to allow for removal prior to x-ray imaging.

Preferably during the treatment the MR magnet is stored in the exterior magnet storage room and the magnet door is closed.

Preferably the storage door of the storage location for the after-loader includes RF shielding arranged so as to prevent RF radiation from the after-loader, which must remain powered, from interfering with the MR imaging.

Preferably the storage location for the after-loader includes a receptacle which receives a plug of the after-loader when in the storage location and the safety system is arranged to confirm that the after-loader is properly stored.

Preferably the safety system is arranged to check that the after-loader plug is in the receptacle and that the storage door is locked before allowing opening of the magnet door.

Preferably once the magnet door is given permission to open, the safety system sends a signal to a lock of the storage door that prevents the storage door from being opened.

The embodiment of this invention for MR-guided brachytherapy includes a patient support and safety system for a movable MRI solution.

The arrangement herein can provide the following advantageous features:

a) it provides MR-guided brachytherapy without moving the patient.

b) it provides MR and X-ray compatible table with MR coil integration to allow efficient transitions from applicator insertion to MR imaging and to treatment delivery.

c) it provides Removable extension back section extension and movable side rails for mounting stirrups for applicator insertion.

d) it provides a safety system to prevent the after-loader from being brought into the bunker while the MR is in the room.

e) it provides MR coils designed for integration into the MR and X-ray compatible table to allow for removal prior to x-ray imaging.

f) it provides a better method for MR-guided brachytherapy by utilizing a movable MRI system that can be brought into the MRI for imaging and applicator insertion, and then removed from the room for x-ray imaging and after-loader treatment delivery. To accomplish this requires the use of safety systems and a novel patient support system designed for brachytherapy applications.

Patient Support Structure:

The patient support structure is an operating room (OR) table that is designed for MR imaging from head to pelvis. This support structure is located in the brachytherapy bunker, and is designed in such a way to enable a movable MR system to move over it for imaging. The design includes a removable extension that interfaces with the back section of the support structure 5-15 cm from the imaging isocenter.

Also included in the design is set of removable side rails that allow for mounting of MR-conditional stirrups. These stirrups can be used for gynecological and rectal applicator insertion, and removed prior to imaging.

The table also provides 180 degree rotation with fixed stops at 90, 180 and 270 degrees. With these positions, it is possible to utilize more of the space in the brachytherapy room for procedures, by performing the treatment and x-ray imaging at different positions.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
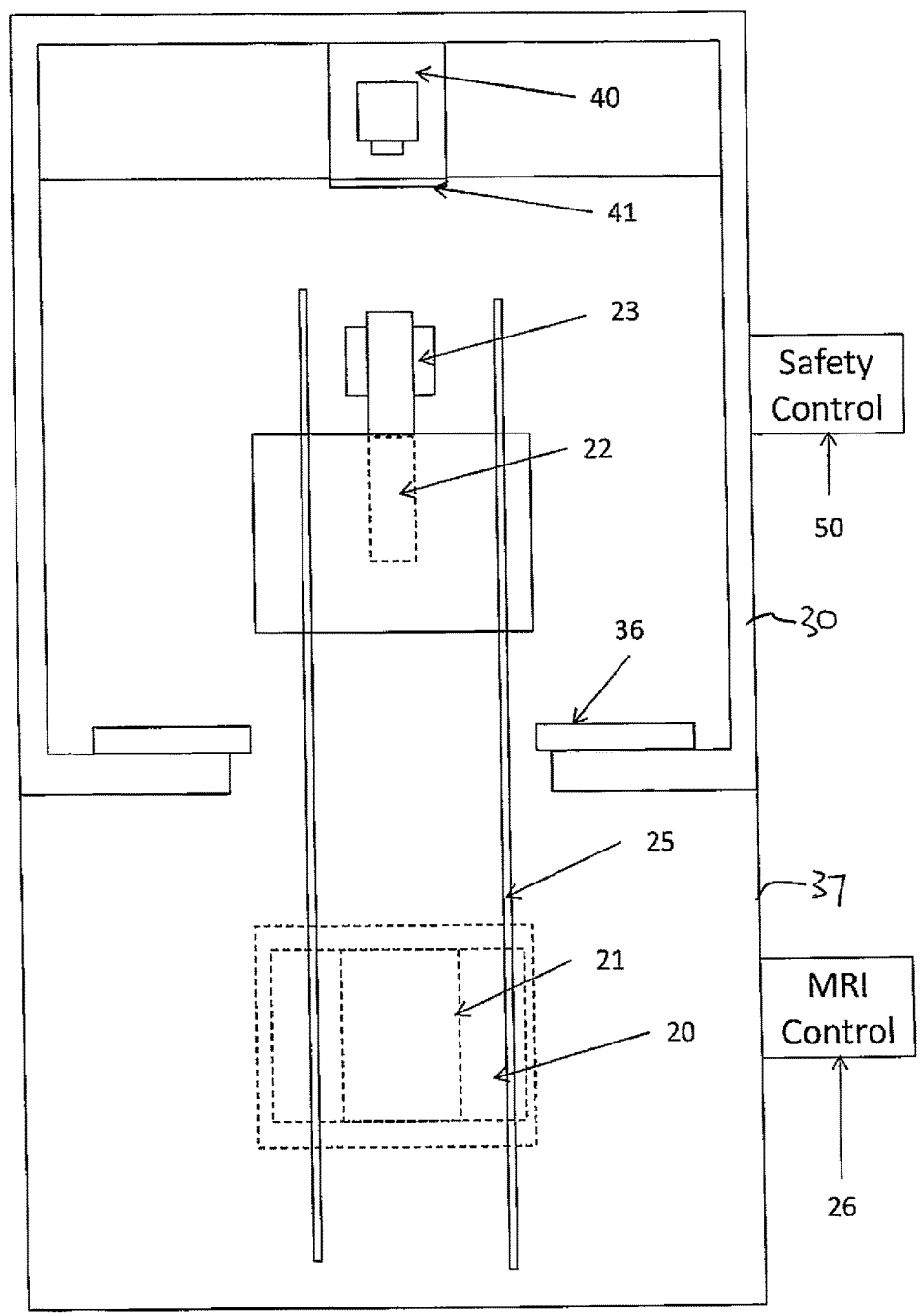
FIG. 1 is a schematic plan view of a brachytherapy room into which a magnet of an MRI system has been moved for imaging.

In FIG. 1 is shown schematically a magnetic resonance imaging system which includes a magnet 20 having a bore 21 into which a patient 22 can be received on a patient table 23. The system further includes an RF transmit body coil 14 which generates a RF field within the bore.

The movable magnet is carried on a rail system 25 with a support suspended on the rail system. Further details of this construction as available from published US application 2008/0039712 published Feb. 14, 2008 assigned to the present assignees, the disclosure of which is incorporated herein by reference.

The system further includes a receive coil system generally indicated at 25A which is located at the isocenter within the bore and receives signals generated from the human body in conventional manner. An MRI control system 26 acts to control the transmit body coil 14 and to receive the signals from the receive coil 25A and to generate an image therefrom.

Figure 2:
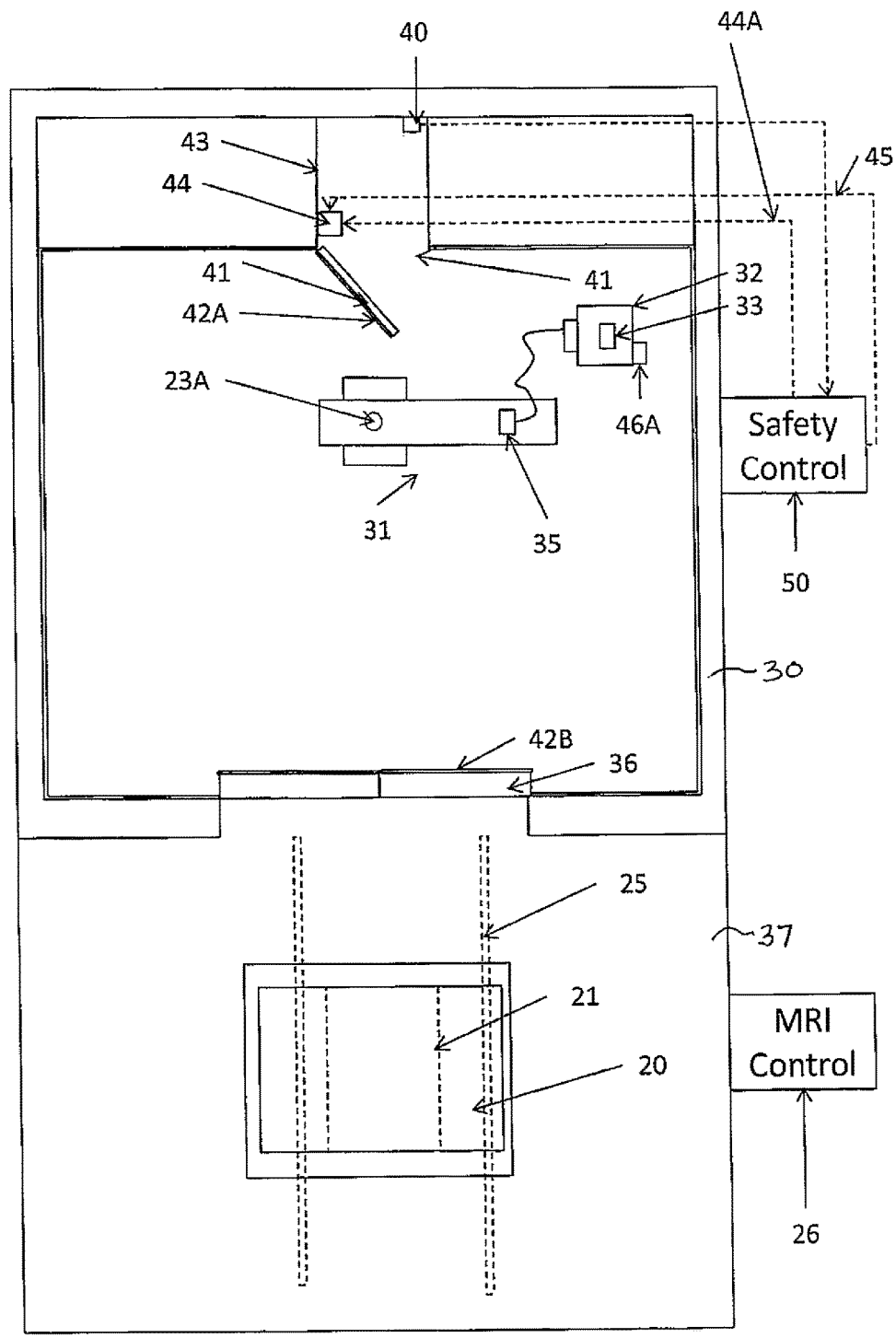
FIG. 2 is a schematic plan view of the brachytherapy room of FIG. 1 into which the magnet of has been removed and the after-loader moved into place.

The MRI system is used in conjunction with a patient radiation therapy system 40 shown better in FIG. 2 with the magnet 20 of the MRI system removed. Thus the therapy system 40 includes a bunker or room 30 within which a patient support 31 is mounted carrying the table 23 and a radiation after-loader 32 is stored. The after-loader 32 carries radiation sources 33 for transferring the radiation to an applicator 35.

The patient having a lesion requiring radiation therapy is placed on the table 23 of the treatment support 31 and prepared for the radiation therapy on the treatment support as described in more detail hereinafter.

During the initial imaging phase, the magnet 20 of the MRI system is carried on the rails 25 into the imaging position at the treatment support for imaging the patient while on the treatment support. The MRI system is used while the patient is on the treatment support to obtain a series of multi-slice 2 dimensional images or 3 dimensional volumetric images of the location of the lesion within the patient and the relative location of the brachytherapy applicator.

The magnet 20 of the MRI system is then moved away from the treatment support 31 through a door 36 of the bunker 30 on the rails 25 into an MR-SIM room 37 or magnet storage area so as to allow the radiation therapy to commence.

The patient support table 23 is MR-conditional, and compatible with the magnet to allow imaging of the region particularly of the lower abdomen. The treatment support table 23 provides 360 degree rotation about a vertical axis with fixed stops at 90, 180 and 270 degrees as shown in FIGS. 1 and 2 where the table is aligned with the magnet bore during imaging and is turned through 90 degrees to a position at right angles to the bore during preparation and treatment. The treatment support table comprises an MR and X-ray compatible table with MR coil integration to allow efficient transitions from applicator insertion to MR imaging and to treatment delivery.

The relative positions of the magnet and the patient support table must be controlled so that the isocenter of the magnet is correctly positioned over the tissue to be irradiated.

The general operation of the system and particularly a safety control system 50 which interlocks the components is shown in FIGS. 1 and 2.

The after-loader 32 is thus located in an RF-shield storage location 40 spaced from the treatment support table closed by a door 41. The control system 50 is provided to control the movements and operation of the components during the imaging and treatment process.

One important aspect to the successful implementation of MR-guided brachytherapy with a movable MRI magnet 20 is a method to ensure that the after-loader 32 is secured and that it is not possible to move it into the bunker 30 while the MR magnet 20 is present. Because the after-loader 32 requires constant power, it must be located outside the radiofrequency shielding layer 42 of the bunker 30 to avoid artifacts in the MR images. The shielding 42 is formed in conventional manner so as to surround the bunker 30 on the inside of the peripheral wall and includes portions 42A and 42B over the door 41 and door 36. In addition there is provided an RF shielded cage 43 inside the storage location 40 that is just large enough to house the after-loader in the storage area 40 when not in use for treatment. The RF-shield surrounding the cage 43 is not essential, only the RF-shielded layer 42A on the door 41.

However, this storage location 40 requires a safety system to prevent the after-loader 32 from being removed while the MR magnet 20 is in the bunker 30. The safety system prevents the after-loader 32 and MR 20 from being in the room simultaneously involves interlocking the after-loader with two elements:

There is provided an after-loader (interlocked) lock 44 for the door 41, which firstly provides a signal 44A to indicate when the door 41 is closed and locked; and, secondly there is provided an input 45 that will dictate when the door can or cannot be unlocked and opened.

There is also provided a dummy cable 46A on the after-loader that has to be plugged into a receptacle 46 into the wall inside the RF cage. The RF cage after-loader plug provides a signal 46B that indicates when the after-loader is in the storage location 40.

A basic workflow to demonstrate how the system functions is, as shown in FIGS. 1 and 2, as follows:

Stage 1 which is the insertion of the needle or applicator 35. The MR magnet 20 is stored in the MR SIM room 37 and the doors 36 between the MR SIM room and the Brachytherapy room are closed.

Stage 2 which is the transition to imaging. The After-loader 32 is in the storage location 40 and the after-loader dummy plug 46A is plugged into the wall outlet 46. The door 41 is locked.

Stage 3 where the Magnet 20 is brought in. The control system 50 checks with RF cage door 41 to see if the after-loader cable is plugged in and if the door is locked. Unless these two conditions are satisfied the doors 36 cannot open. The magnet motion will be also prevented if these doors are closed.

Once the doors 36 are given permission to open, they send a signal 45 to the lock 44 that prevents the door 41 from being opened.

The MR magnet 20 is moved into the room 30, and an interlock prevents the doors 36 from closing with the magnet 20 inside. All MR imaging in the brachytherapy room is performed with the doors 36 open.

Stage 4 where the MR Magnet 20 is returned to the room 37. After MR imaging is complete, the magnet is moved out of the room 30 to MR SIM room 37. The doors 36 are closed. Once the doors 36 are closed, they provide a signal 45 indicating that it is OK to unlock the door 41. The after-loader dummy cable 46A can be removed from the receptacle 46, and the after-loader 32 is able to move out of the storage location 40. The after-loader is available to be used for treatment.

Stage 5 which is the transition to the next patient. The After-loader 32 is returned to the storage location 40, and dummy cable 46 plugged into the wall 46. The door 41 is closed and locked.

The use of MR-guided brachytherapy with a movable MR system provides a robust patient position between applicator insertion, MR imaging and remote after-loader treatment. With a streamlined workflow and consistent positioning, it is possible to improve delivery of brachytherapy treatment for a number of different clinical applications: prostate, cervix, vagina, rectum, esophagus, and lung. The after-loader interlock prevents the possibility of the after-loader and MR system from being in the bunker at the same time.

Figure 3:
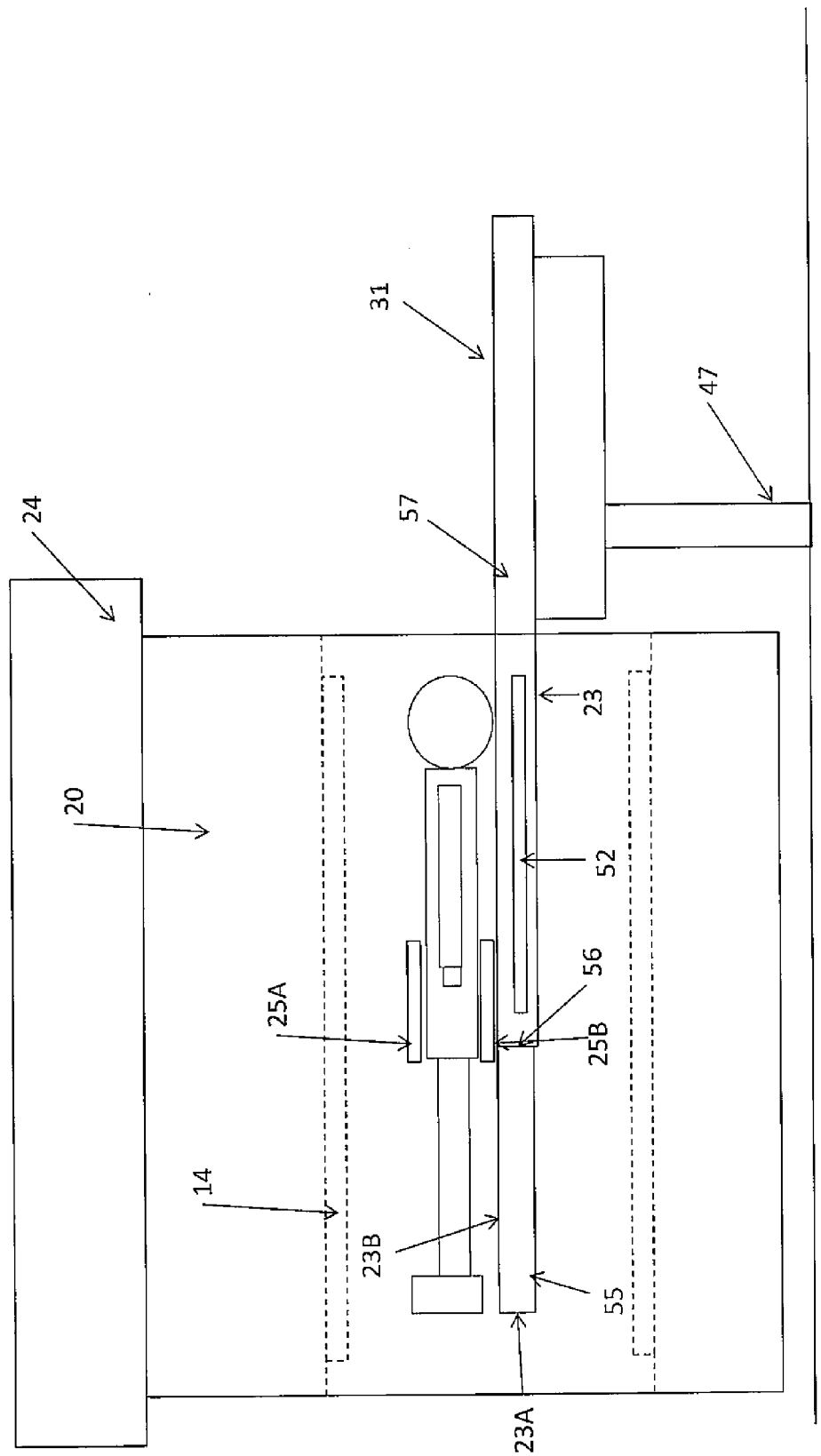
FIG. 3 is a side elevational view of the brachytherapy table of FIG. 1.
Figure 4:
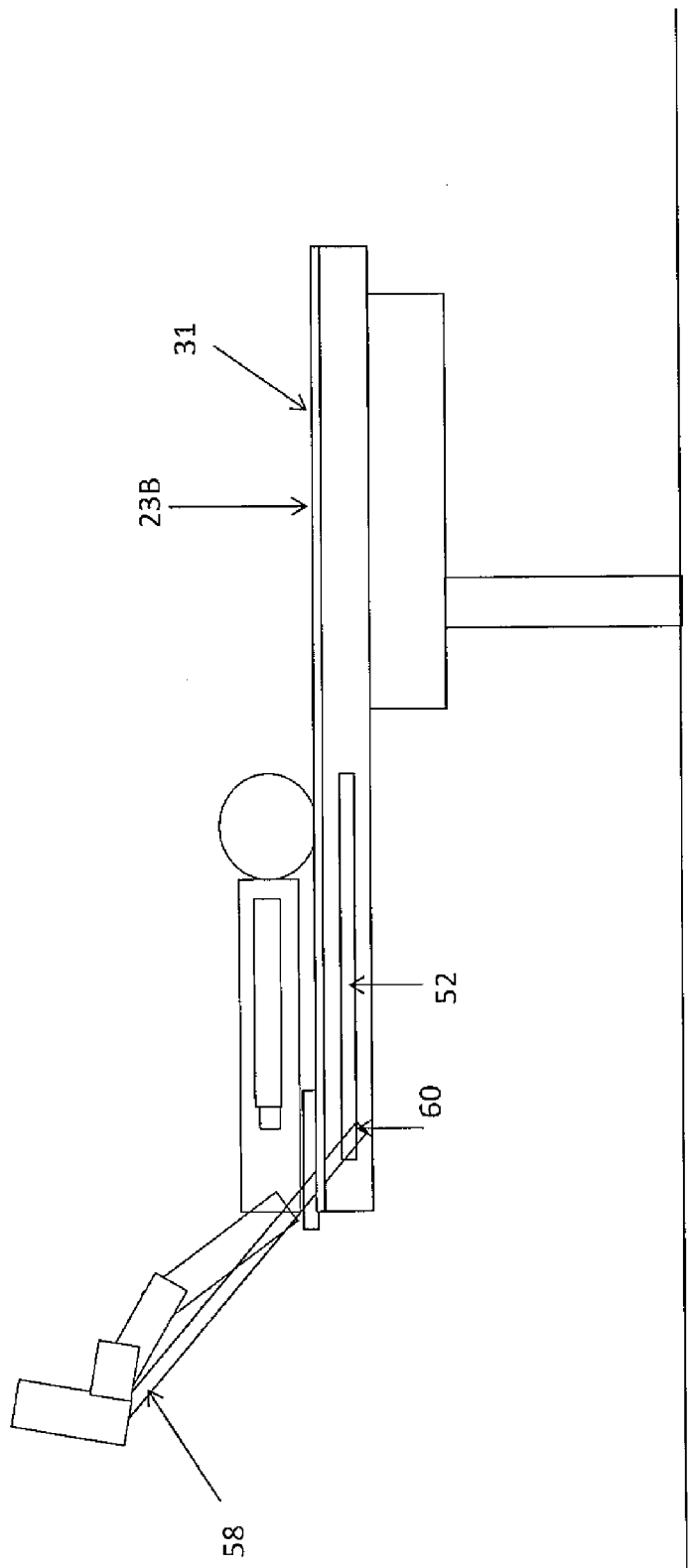
FIG. 4 is a side elevational view of the brachytherapy table of FIG. 1 with the extension piece removed, with legs in stirrups for the applicator insertion.

Turning now to the patient support table, this is shown in FIGS. 3 and 4 which is an overall summary of the brachytherapy table. The Patient Handling System or support table 31 includes a base 47 of a conventional construction which allows the base to move a patient support portion 23 to required locations in height and in orientation. Suitable drive mechanisms and couplings are known in the art and thus are not required to be described herein. At the top of the base 47 is mounted the patient support portion 23 in the form of a generally planar body formed of a fiber reinforced plastics material so as to define a surface area sufficient for supporting the patient while lying on the patient support portion. The patient support 23 includes a rear edge 23A at or beyond the feet of the prone patient together with two side edges spaced by a distance sufficient to receive and contain the legs, body and arms of the patient to be supported by the support portion.

On top of the patient support portion 23 is provided a mattress 23B which is shaped to overlie the patient support portion 23. The portion of the table top 23 to be inserted into the bore is cantilevered forward from the base 47.

The structural support for the patient is provided by the support portion 23 which is formed of a fiber reinforced resin material where the fibers are laid in sheets and infused by the resin material to provide a flat structural member of sufficient strength to carry the weight of the typical patient. In order that the patient support portion be formed of a material which does not interfere with the operation of the magnet or the generation and acquisition of the necessary signals used in magnetic resonance imaging, the fiber reinforcement selected for use in the structure of the portion 23 is a fiber which has sufficient strength to provide the necessary resistance to bending but a fiber which is non-electrically conductive. Thus carbon fibers cannot be used since long carbon fibers generate or allow currents to flow within the structure of the portion and such currents will interfere with the necessary signals. The currents are generated by the radiofrequency signals and changing magnetic field gradients, which are generated within the magnet for use in the magnetic resonance imaging. Typically aramid fibers such as Kevlar™ can be used in replacement for the carbon fibers typically used in such structures.

The mattress 23B is formed of a stiff foam material encased by a skin to provide an exterior surface which is resistant to fluids and can be readily cleaned for sterilization to be used in clinical situations.

Where the imaging is to be of the lower abdomen, the anterior body phased-array receive coil 25A is arranged to be placed on top of the body of the patient when in place for imaging on the mattress and also the posterior coil 25B is arranged to be inserted into a receptacle in the tabletop underneath the patient.

The table top portion 23 includes a pair of side rails 52 each extending along a respective side of the top portion from a forward end adjacent the head of the patient to a rearward end adjacent the legs and feet of the patient. The side rails are fastened to the sides of the top portion 23 by connectors which hold the two sections fastened to the table to 23 at a position spaced away from the side edges.

The table top portion 23 includes a removable end-section or extension 55 which is attached to the main portion by a coupling shown only schematically at 56. In an alternative arrangement, the extension can be removed from the operating position by acting to swing down on hinges instead of being removed completely. The core of the concept is simply to move the end-portion out of the way so that the oncologist can have full access to the pelvic region.

Thus in operation, a main section 57 of the tabletop 23 supports the patient during MR imaging and treatment.

As shown in FIG. 4, the removable side rails 52 are used for mounting stirrups 58 during procedures. The stirrups 58 form standard commercially available stirrups for elevating the legs for the brachytherapy applicator insertion.

In FIG. 4 the brachytherapy tabletop extension 55 is removed while the legs are supported in the stirrups 58 to provide the oncologist with complete access to the pelvic region for inserting the brachytherapy applicators. The extension 55 is removed by separating the coupling 56 which can be designed for easy removal or swing down but also providing sufficient connection that the extension forms a cantilevered portion from the bottom end of the main portion of the table.

In FIG. 4 there is shown the region of pelvic access available to the oncologist for the brachytherapy applicator insertion following the removal of the brachytherapy tabletop extension 55. The attachment point 60 for the stirrups to the removable OR table side rails 52 is of a conventional arrangement.

As shown in FIG. 3, the extension piece 55 is put back in position, the legs of the patient are lowered from the stirrups onto the extension portion 55 after applicator is secured with the applicator support stand, and the stirrups 58 are removed.

A support stand (not shown) can be provided that rests under the patient's legs to keep the support in place during MR imaging and treatment and includes an applicator support stand arm that secures the brachytherapy applicator 35.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method for guiding brachytherapy radiation treatment of a lesion of a patient comprising:
   supporting the patient on a treatment support table;
   while the patient is supported on the support table, preparing the patient for radiation therapy on the treatment support table and moving an applicator for applying the brachytherapy radiation treatment to a treatment position at the patient;
   providing an after-loader for supplying a radiation source to the applicator in a storage location having a storage door;
   with the applicator located at the treatment position, moving the after-loader from the storage location to the applicator;
   locating the treatment support table and the after-loader forming a radiation therapy treatment system in a treatment room;
   providing an MRI system for imaging the patient including a cylindrical magnet;
   moving the after-loader in the treatment room to the storage location spaced from the treatment support table;
   providing an opening from an exterior magnet storage room into the treatment room with a magnet door on the opening;
   with the after-loader moved to the storage location, moving the cylindrical magnet of the MRI system from the exterior magnet storage room outside the treatment room through the opening with the magnet door open into a position surrounding the treatment support table for obtaining images of the patient while on the treatment support table;
   while the patient is on the treatment support table, using the MRI system to obtain a series of images of a location of the lesion and the applicator at the treatment position within the patient;
   moving the magnet of the MRI system away from the treatment support table and out of the treatment room through the opening, and closing the magnet door so as to allow the radiation therapy;
   providing a safety system to control movement of the after-loader and the magnet;
   and using the images of the patient to locate the applicator with respect to the patient.

2. The method according to claim 1 wherein the treatment support table comprises a first main portion for supporting the upper body of the patient up to and including the patient's pelvic region and a second removable extension portion, extending from an end of first main portion to the patient's feet.

3. The method according to claim 2 wherein the second removable extension portion is cantilevered from the end of the first main portion.

4. The method according to claim 3 wherein the first main portion terminates at the second removable extension portion leaving an area open for access by a physician.

5. The method according to claim 2 wherein the first main portion is arranged for attachment of stirrups for supporting the feet of the patient with the second removable extension portion removed or swung down such that the applicator is inserted by a physician to a required location with the second removable extension portion removed or swung down and the feet in the stirrups.

6. The method according to claim 5 wherein the stirrups are carried on side rails of the first main portion.

7. The method according to claim 6 wherein the stirrups are removed and the second removable extension portion is replaced or swung back up into place for connection of the after-loader to the applicator for treatment.

8. The method according to claim 5 wherein the stirrups are removed for imaging.

9. The method according to claim 5 wherein MR-conditional stirrups remain in place for imaging and are arranged for insertion into a bore of the cylindrical magnet.

10. The method according to claim 1 wherein the patient with the applicator installed at the treatment position is imaged by the MRI system to ensure proper location of the application.

11. The method according to claim 1 wherein the imaging and the brachytherapy radiation treatment are carried out without moving the patient relative to the treatment support table.

12. The method according to claim 1 wherein the treatment support table comprises an MR and X-ray compatible table with MR coil integration to allow efficient transitions from applicator insertion to MR imaging and to x-ray imaging and treatment delivery.

13. The method according to claim 1 wherein the safety system is arranged to prevent the after-loader from being brought from the storage location into the treatment room while the cylindrical magnet is in the treatment room.

14. The method according to claim 1 wherein there are provided MR coils designed for integration into the treatment support table to allow for removal prior to x-ray imaging.

15. The method according to claim 1 wherein the cylindrical magnet is stored in the exterior magnet storage room and the magnet door is closed during said treatment.

16. The method according to claim 1 wherein the storage door of the storage location for the after-loader includes RF shielding arranged so as to prevent RF radiation from the after-loader from interfering with obtaining the series of images using the MRI system.

17. The method according to claim 1 wherein the storage location for the after-loader includes a receptacle which receives a plug of the after-loader when in the storage location and the safety system is arranged to confirm that the after-loader is properly stored.

18. The method according to claim 17 wherein the safety system is arranged to check that the after-loader plug is in the receptacle and that the storage door is locked before allowing opening of the magnet door.

19. The invention according to claim 18 wherein, once the magnet door is given permission to open, the safety system sends a signal to a lock of the storage door that prevents the storage door from being opened.

20. The method according to claim 1 wherein the treatment support table provides 270 degree rotation about a vertical axis with fixed stops at 90, 180 and 270 degrees.

* * * * *